US005391713A

United States Patent [19]

Borg

[11] Patent Number: 5,391,713

[45] Date of Patent: Feb. 21, 1995

[54] INTERFERON PURIFICATION PROCESS

[75] Inventor: Håkan Borg, Umeå, Sweden

[73] Assignee: Bionative AB, Umea, Sweden

[21] Appl. No.: 66,655

[22] Filed: May 25, 1993

Related U.S. Application Data

[63] Continuation of Ser. No. 778,804, Dec. 18, 1991, abandoned.

[30] Foreign Application Priority Data

Jun. 20, 1989 [SE] Sweden ................................ 8902230

[51] Int. Cl.[6] ........................ C07K 15/26; C07K 3/20; A61K 45/02

[52] U.S. Cl. .................................. 530/351; 424/85.4; 424/85.7

[58] Field of Search ............... 530/351; 424/85.4, 85.7

[56] References Cited

U.S. PATENT DOCUMENTS

| | | | |
|---|---|---|---|
| 3,414,651 | 12/1968 | Fantes | 424/85.5 |
| 4,474,754 | 10/1984 | Shimizu et al. . | |
| 4,873,312 | 10/1989 | Arakawa | 424/85.5 |

FOREIGN PATENT DOCUMENTS

| | | |
|---|---|---|
| 457352 | 12/1988 | Sweden . |
| WO80/02229 | 10/1980 | WIPO . |
| 8002229 | 10/1980 | WIPO . |

*Primary Examiner*—Howard E. Schain
*Assistant Examiner*—Lynn Touzeau
*Attorney, Agent, or Firm*—Burns, Doane, Swecker & Mathis

[57] ABSTRACT

A process for purification of human leukocyte interferon is described. The process includes immunoaffinity chromatography, ion-exchange chromatography, and a series of precipitation and centrifugation steps.

25 Claims, No Drawings

INTERFERON PURIFICATION PROCESS

This application is a continuation of application Ser. No. 07/778,804, filed Dec. 18, 1991, now abandoned.

The present invention relates to a process for the purification of a crude human leukocyte interferon.

Interferons are a group of proteins naturally produced in the body in response to an exterior stimulus, for example virus causing an infection. Interferon may also be present in small quantities in the blood in connection with certain virus and tumor diseases. Interferons are formed in the body as part of the defense against infection and is considered to constitute an immediate defense mechanism in the protection against a virus infection.

Several types of interferons are known. As examples there may be mentioned $\alpha$-Interferon produced by leukocytes, $\beta$-Interferon produced by binding tissue cells and gamma-interferon produced by immuno-competent cells.

Native interferon produced from leukocytes consists of a native mixture of different $\alpha$-interferon subtypes or interferon components. The different interferon components are named Interferon $\alpha$-1, Interferon $\alpha$-2, Interferon $\alpha$-3 etc. Moreover, there is an allelic variation within the different $\alpha$-interferon components named Interferon $\alpha$-2a, $\alpha$-2b, $\alpha$-2c etc.

Interferon produced from leukocytes according to the "Cantell method", so called PIF-Interferon or Cantell-Interferon has been used since 1971 in the treatment of different virus and tumor diseases. The expectations on interferons as a drug against different tumor and virus diseases arising during the 1970:ies are exclusively based on clinical results obtained in the use of Cantell-Interferon.

In the early 1980:ies interferon was cloned and interferon manufactured using recombinant-DNA-techniques is today a drug in some fifty countries.

Native interferon manufactured from leukocytes consists of a mixture of some twenty different $\alpha$-interferons. Recombinant interferon consists of a cloned $\alpha$-interferon subtype.

The present invention resides in new techniques for the purification of native leukocyte interferon. The original Cantell-interferon originally manufactured in Finland in the early 1970:ies has a relatively low purity, of the order of 1%. As such, it is useful but leaves much to be desired due to today's stringent requirements as to purity and reproducibility of drugs.

The present invention has for a main purpose to provide a process for the manufacture of a highly purified leukocyte interferon for clinical use.

Another object of the invention is to provide such purification process which is highly reproducible, relatively inexpensive and provides for relative ease of performance.

For these and other objects which will be clear from the following description the present invention resides in a process for the purification of a crude human leukocyte interferon, said process comprising the following steps:

a) applying a solution of said crude interferon onto an immuno-affinity adsorption column;
b) eluting the adsorbed interferon from said column using a buffer solution;
c) concentrating the eluate resulting from step b) with a thiocyanate solution by either precipitation or an exchange chromatography; and
d) recovering the precipitated interferon obtained in step c).

In such process it is preferred to use for the preparation of an immunoaffinity adsorption column a recombinant interferon for the generation of the antiserum from which polyclonal antibodies are isolated and covalently attached to the column matrix.

The process of the invention is preferably performed using a further step of concentrating the eluate from the immuno affinity adsorption column using an ion exchange column. The interferon is suitably eluted from such ion exchange column by increasing the pH. Such pH increase can be obtained by applying a buffer solution to the column.

In addition to the precipitation step using for example a thiocyanate solution the process may involve another precipitation step, wherein the interferon resulting from such precipitation is again precipitated in ethanol before its recovery.

After the single or double precipitation the interferon obtained is preferably made subject to gel filtration, and the proper effluent fractions having absorbance at 280 nm are collected and recovered.

In the precipitation step it is preferred to use a solution of potassium thiocyanate. Other precipitants are trichloroacetic acid and ammonium sulphate. Elution of the interferon from the ion exchange column to concentrate the eluate from the preceding step is suitably performed by applying a buffer solution to increase the pH. Such pH increase is preferably carried to a pH above neutral, such as to about 8 or higher.

The invention also covers a purified human leukocyte interferon whenever prepared by the process described herein.

The present invention will now be further illustrated by specific examples, which, however, are not to be construed as limiting the scope of the invention otherwise than as defined in the appended claims.

EXAMPLE 1

Preparation of antiserum

In the production of antiserum healthy goats not previously immunized are used. The antigen used in the immunization is a recombinant interferon, $\alpha$-88, manufactured at the University of Umea and described in detail in published European Patent Application No. 86903650.9, publication No. 0 263 102. This recombinant interferon is dissolved in physiologic phosphate buffer, the specific activity of the solution being about $2\times10^{8}$ IU/mg. This solution is administered to the goats together with "Freund's complete adjuvant" at the initial immunization. Then immunization using "Freund's imcomplete adjuvant" is performed once per week or every fortnight in volumes of from 0.2 ml to 1.0 ml.

The goats are bled via the jugular vein every fortnight after the third immunization. The drained blood is investigated with regard to contents of anti-interferon antibodies and unspecific binding. The contents of antibodies is analyzed using an assay measuring neutrilizing titre, i.e. the titre measuring the amount of interferon which is inactivated by the antibodies in an interferon-sensitive biologic system. Specific and unspecific binding is measured by conventional "Western blot".

150–200 ml blood is normally bled each time. The fresh blood is kept for 24 hours in the refrigerator and coagulates during this period. The blood is then centrifugated and the serum is recovered. This serum containing antibodies against interferon is made subject to further purification as described below.

EXAMPLE 2

Preparation of immuno-affinity adsorption column

The antiserum obtained in Example 1 is precipitated with 25 ammoniumsulfate/100 g antiserum with slow agitation in centrifuge bottles which are left over night. The following day the antiserum is centrifuged at 4000 g for 30 min. The supernatent is discarded and the precipitate is washed twice with ammonium sulfate 1.75 mol/l to decrease the amount of hemoglobin and albumin. The precipitate is transferred to dialysis tubing and dialysis is performed alternately against water and sodium acetate buffer 0.05M NaAc, 0.021M Hac, pH 5.0.

During dialysis a precipitate forms consisting of lipoproteins, the precipitate being removed by centrifugation at 4000 g for 30 min. The supernatent containing gammaglobulins is applied to a column containing DEAE Sepharose® FF (25 ml packed gel/100 ml crude antiserum) equilibrated with acetate buffer, pH 5.0. The dialysed antiserum is passed through the column and eluted with about one column volume of acetate buffer.

Volume: 445 ml
Absorbance 280 nm: 35.2
IgG conc: 25.3 mg/ml
Total IgG: 11.3 g
Recovery: 16 mg IgG/ml serum The immunoglobulin containing eluate is dialysed against coupling buffer, sodium bicarbonate 0.1 mol/l and sodium chloride 0.5 mol/l.

Br-CN-activation of Sepharose 4B

Sepharose is washed with distilled water on a glass funnel and sucked dry. About 40–60 g gel/g IgG is weighed out and suspended in potassium phosphate buffer 2 mol/l pH 11.0. The gel slurry is cooled on an ice-bath. BrCN is dissolved in water 0.05–0.1 g BrCN/ml. 3.3 g BrCN/100 g dry sucked gel is added and the sepharose is activated for 10 min under gentle stirring on a magnetic stirrer. The gel slurry is transferred to a glass funnel and washed with cold distilled water until neutral reaction of eluate. The activated gel is mixed with the immunoglobulin solution and incubated at room temperature over night under gentle agitation.

The gel is transferred to a glass funnel and the filtrate is analyzed for protein content by measurement of $A_{280}$. The gel is again suspended in coupling buffer and glycin 0.1 mol/l is added to block remaining coupling sites and the gel is incubated for at least 1 hour at room temperature. After the blocking procedure the gel is repeatedly washed with phosphate buffer 0.02 mol/l sodium chloride 0.2 mol/l pH 7.0 and citric acid 0.1 mol/l sodium chloride 0.15 mol/l. The gel is stored in phosphate buffered saline with 0.04% sodium azide as preservative.

Coupling procedure 750 ml Sepharose 4 B is washed with 2.5 l distilled water on a glass funnel and sucked dry, the weight of the "dry" gel is 520 g. The gel is resuspended in 500 ml potassium phosphate buffer 2.0 mol/l pH 11.0 and cooled on an ice-bath. 17.3 g BrCN is dissolved in 200 ml water and added to the gel slurry and the gel is activated for 10 min. The gel is washed with 7 l cold distilled water. The reaction of the eluate is neutral.

The gel is mixed with the immunoglobulin fraction dialyzed against coupling buffer, sodium bicarbonate 0.1 mol/l sodium chloride 0.5 mol/l pH 8.5 and incubated over night at room temperature. The following day the gel is filtred and washed with one volume of coupling buffer and the protein concentration in filtrate and wash is determined by means of $A_{280}$.

$A_{280}$ filtrate: 184 mg protein
$A^{280}$ wash: 165 mg protein
totally: 349 mg protein
Coupling efficiency: 96.9%

The gel is resuspended in coupling buffer with glycin 0.1 mol/l to block remaining activated sites for 1 hour. The gel is washed with phosphate buffer pH 7.0 and citric acid. The gel is stored in phosphate buffer saline with 0.04 sodium azide as preservative.

EXAMPLE 3

Production of crude Interferon

In this production buffy coats are used to prepare crude interferon. Buffy coats is a waste product at the ordinary blood banking in hospitals. The buffy coats used are no older than 48 hours and most of the buffycoats are not older than 24 hours.

To prepare leukocytes from buffy coats the red blood cells thereof are lyzed by addition of ammonium chloride to a final concentration of 0.83%. After 10 min at room temperature the leukocytes are centrifuged in a basket centrifuge with a flow rate of 300 ml/min. The leukocytes are suspended in PBS. The process is repeated once and the leukocytes obtained are then added to the culturing media.

The purified leukocytes are suspended in Eagels mem with the following additives:

Neomycin 25 μg/ml
Tricine 3 mg/ml
4% human plasma precipitated with 6% Polyethylene glycol 6000 (Inglot A et al, Acta Virol. 19; 250–254, 1975)

The use of PEG-fractionated plasma instead of α-gamma serum is the only major difference from the original Cantell-method. The cells are used at a concentration of about $10^7$ cells per ml in 4 l round bottles containing approximately 2.0 l each. Magnetic stirring is performed on the water bath at 37° C. The cell culture is primed through addition of crude leukocyte interferon 100 IU/ml. After 2 hours of priming Sendai virus, about 150 haemaglutinating units per ml (about 40 ml Sendai virus per liter) is added. After 20 hours at 37° C. the leukocytes are removed by centrifugation or filtration. The crude interferon will be stored maximum 7 days before purification.

EXAMPLE 4

Concentration of crude Interferon

The crude interferon solution obtained according to Example 3 is concentrated by ultrafiltration using a Filtron system, MW 10,000 filter. Before the ultrafiltration takes place, the crude interferon is filtered through a 0.45 μm membrane (Millipore, Prostak) to remove cells and cell debris. The interferon solution is concentrated about 5 times.

EXAMPLE 5

Affinity chromatography of crude Interferon

The affinity column (BP 113/15, Pharmacia, gel volume: about 1 l) obtained as described in Example 2 is equilibrated with 0.02M Tris-HCl 0.2M NaCl 0.001M EDTA pH 8.0 (Tris-buffer). The interferon solution obtained from Example 4 is then allowed to pass the column at a flow rate of about 4 l per hour. After the interferon solution has passed the column, the column is washed using Tris-buffer until the absorbance of the eluate is zero or nearly zero.

The affinity column is desorbed by passing 0.1M citric acid 0.15M NaCl pH 2.0. The citric acid buffer is passed through the column at a flow rate of about 3 l per hour. This acidification of the column results in desorption of the interferon taken up via the column. The desorption is continued until absorbance at 280 nm ceases and the collected interferon solution is recovered. The volume is about 5 l.

EXAMPLE 6

Concentration of desorbed Interferon

The interferon resulting from the desorption according to Example 5 is passed through an ion exchange column (S-Sepharose®) equilibrated with citric buffer, pH 2.0. The ion exchanger is then washed using citric buffer, and the interferon is eluted by increasing pH through the addition of Tris-buffer resulting in an pH increase to about pH 8.

EXAMPLE 7

Precipitation of Interferon using potassium thiocyanate

The interferon solution obtained from Example 6 is carefully added with 5M KSCN and human serum albumin (HSA) under stirring to a final concentration of 0.5M KSCN (weight ratio Ifn:HSA about 1:5–10). Hydrochloric acid (1M) is then added until the pH has decreased from about 8 to about 2.0. The cloudy precipitation is centrifuged at 5000 r/min for 30 min (Beckman J-21). The supernatant is carefully recovered.

EXAMPLE 8

Precipitation with Ethanol

The interferon precipitate from the sodium thiocyanate precipitation in Example 7 is slurried in 95% acid ethanol together with HSA (weight ratio Ifn to HSN about 1:5–10) (about 300 ml) having a temperature of −20° C. The slurry is centrifuged for 30 min at 5000 r/min. The supernatant containing the interferon is recovered and the pH thereof is gently increased to pH 8.0 by adding 0.1M NaOH. The precipitate is then centrifuged for 30 min at 5000 r/min (Beckman J-21). The supernatant is decanted and the precipitate is dissolved in 10 ml 0.15M sodium phosphate buffer +0.5M KSCN, pH 8.0

EXAMPLE 9

Gel filtration of precipitate

The interferon solution obtained from Example 8 is centrifuged and made subject to gel filtration on a column (AcA-54, IBF, France, 2.5×90 cm). The interferon peak is then recovered, detected with UV-light, 280 nm. The purity of the interferon obtained is about 80% and when assayed (Western blot) it is found to contain all interferon components present in the Cantell-type crude interferon starting material.

The process of this invention offers many advantages, among which there may be mentioned:

efficient elimination of the riks for virus infection, high yield, simple and reliable performance.

The examples given above are not to be construed as limiting the scope of the invention. They have been presented merely for purposes of illustration and description of the invention. Obviously, many modifications and variations are possible to the skilled artisan in the light of the invention as described. It is intended that the scope of the invention shall be defined by the appended claims.

I claim:

1. A process for the purification of a crude human leukocyte interferon comprising the steps:

a) applying a solution of said crude interferon onto an immuno-affinity adsorption column;

b) eluting the adsorbed interferon from said column using a buffer solution of acid pH;

c) concentrating the eluate resulting from step b) with a thiocyanate solution by either precipitation or ion exchange chromatography;

d) precipitating the interferon present in the concentrated eluate resulting from step c) with a thiocyanate solution;

e) reprecipitating the interferon resulting from step d) in aqueous ethanol; and f) recovering the interferon obtained in step e).

2. A process according to claim 1, wherein the eluate from step b) is concentrated using an ion exchange column, the interferon being eluted from said column by increasing the pH to a pH above neutral by applying a buffer solution to the column.

3. A process according to claim 1, wherein the eluate from step b) is concentrated by precipitation using thiocyanate, trichloroacetic acid or ammonium sulphate.

4. A process according to claim 1, wherein the inteferon resulting from step f) is further purified by gel filtration, and the effluent showing absorbance at 280 nm is then recovered.

5. A process according to claim 1, wherein the column used in step a) contains polyclonal antibodies obtained by immunization using a recombinant interferon.

6. A process according to claim 1, wherein the precipitation in step c) is performed with a solution of potassium thiocyanate.

7. a process according to claim 1, wherein the precipitation of step c), d), and/or e) is effected in the presence of albumin.

8. A process according to claim 2, wherein the interferon resulting from step f) is further purified by gel filtration, and the effluent showing absorbance at 280 nm is then recovered.

9. A process according to claim 3, wherein the interferon resulting from step f) is further purified by gel filtration, and the effluent showing absorbance at 280 nm is then recovered.

10. A process according to claim 2, wherein the column used in step a) contains polyclonal antibodies obtained by immunization using a recombinant interferon.

11. A process according to claim 3, wherein the column used in step a) contains polyclonal antibodies obtained by immunization using a recombinant interferon.

12. A process according to claim 4, wherein the column used in step a) contains polyclonal antibodies obtained by immunization using a recombinant interferon.

13. A process according to claim 2, wherein the precipitation in step c) is performed with a solution of potassium thiocyanate.

14. A process according to claim 3, wherein the precipitation in step c) is performed with a solution of potassium thiocyanate.

15. A process according to claim 4, wherein the precipitation in step c) is performed with a solution of potassium thiocynate.

16. A process according to claim 2, wherein the precipitation of step c), d), and/or e) is effected in the presence of albumin.

17. A process for purification of a crude human leukocyte interferon composition, comprising the steps:

a) applying a crude human leukocyte interferon composition to an immunoaffinity column comprising anti-human leukocyte interferon antibodies;

b) washing the column with a buffer;

c) desorbing the human leukocyte interferon from the immunoaffinity column using an acidic buffer solution at a pH of about 2.0;

d) applying the resultant desorbed human leukocyte interferon containing composition to an ion exchange column;

e) eluting the human leukocyte interferon from the ion exchange column by increasing the pH through the addition of Tris-buffer until the resultant pH is about 8;

f) precipitating interferon from the resultant eluate by the addition of a potassium thiocyanate solution;

g) reprecipating interferon from the resultant sodium thiocyanate precipitate using acidic ethanol having a temperature of about −20° C.;

h) adding to the resultant supernatant a basic solution until the resultant pH is about 8.0;

i) centrifuging the resultant precipitate and dissolving in a sodium phosphate buffer/KSCN solution; and j) subjecting the resultant interferon solution to centrifugation followed by gel filtration on a column to recover a product which exhibits an absorbance at 280 nm.

18. The process of claim 17 wherein the antibodies bound to the immunoaffinity column are produced using recombinant human leukocyte interferon as the immunogen.

19. The process of claim 17 wherein the immunoaffinity column comprises a sepharose column.

20. The process of claim 17 wherein the washing step (b) is effected until the absorbance of the eluate is about zero.

21. The process of claim 17 wherein the crude interferon applied to the immunoaffinity column is obtained from leukocytes obtained from buffy coats.

22. The process of claim 21 wherein the crude interferon is concentrated by ultrafiltration prior to application to the immunoaffinity column.

23. The process of claim 17 wherein the acidic ethanol is 95% acid ethanol.

24. The process of claim 17 wherein the acidic ethanol comprises human serum albumen.

25. The process of claim 17 wherein the ion exchange column comprises a sepharose column.

* * * * *